United States Patent [19]

Umemoto

[11] Patent Number: 5,081,249

[45] Date of Patent: Jan. 14, 1992

[54] N-FLUOROPYRIDINIUM-SULFONATES AND A PROCESS FOR THEIR PREPARATION

[75] Inventor: Teruo Umemoto, Tsukuba, Japan

[73] Assignees: Sagami Chemical Research Center, Tokyo; Onoda Cement Company, Ltd., Onoda, both of Japan

[21] Appl. No.: 650,496

[22] Filed: Feb. 5, 1991

Related U.S. Application Data

[63] Continuation-in-part of Ser. No. 296,411, Jan. 9, 1989, Pat. No. 4,996,320, which is a continuation of Ser. No. 22,275, Mar. 5, 1987, abandoned, which is a continuation-in-part of Ser. No. 870,010, Jun. 3, 1986, abandoned.

[51] Int. Cl.[5] .................. C07D 213/62; C07D 213/71

[52] U.S. Cl. .................... 546/294; 546/294; 546/345; 546/347

[58] Field of Search ............... 546/294, 295, 347, 345

[56] References Cited

PUBLICATIONS

Chemical Abstracts, vol. 113, No. 25, Abst. No. 230, 395-P Dec. 17, 1990.

*Primary Examiner*—Alan L. Rotman
*Attorney, Agent, or Firm*—Olson & Hierl

[57] ABSTRACT

A class of N-fluoropyridinium-sulfonates is provided along with a processw for making same. Starting pyridine sulfonic acids and acid salts are fluorine substituted at the pyridine nitrogen atom with dilute gaseous fluorine under liquid phase contacting conditions. The N-fluorine substituted products are excellent fluorinating agents which exhibit high specificity.

3 Claims, No Drawings

N-FLUOROPYRIDINIUM-SULFONATES AND A PROCESS FOR THEIR PREPARATION

CROSS-REFERENCE TO RELATED APPLICATIONS

This application is a continuation-in-part of Ser. No. 296,411, filed Jan. 9, 1989, now U.S. Pat. No. 4,996,320, which is a continuation of Ser. No. 022,275, filed Mar. 5, 1987, now abandoned, which in turn is a continuation-in-part of Ser. No. 870,010, filed June 3, 1986, now abandoned.

FIELD OF THE INVENTION

The present invention relates to certain N-fluoropyridinium-sulfonates and processes for their preparation.

BACKGROUND OF THE INVENTION

N-Fluoropyridinium salts including N-fluoropyridinium trifluoromethanesulfonate have previously been reported as useful fluorinating agents. (*Tetrahedron Lett.*, 27, 4465 (1986) and Japanese Patent Laid-Open No. 63-10764.) However, the use of such fluorinating agents does not always provide satisfactory selectivity with regard to the reaction positions in the product.

For example, when phenol is fluorinated using N-fluoropyridinium trifluoromethanesulfonate, three components of o-fluorophenol, p-fluorophenol and 2,4-difluorophenol are produced. (Japanese Patent Laid-Open No. 63-10764, Reference Example 1). When this compound is used to fluorinate a trimethylsilylenol ether derivative of a steroid, not only the 6-fluorosteroid (which is fluorinated at the 6-position and which is important as a physiologically active substance) but also the 4-fluorosteroid (which is fluorinated at the 4-position) are produced in a ratio of about 2.3:1. (Japanese Patent Laid-Open No. 63-10764, Reference Example 37).

Since the process for separating and purifying each of the isomers is complicated, the yield and overall efficiency of the process is low. Production methods which produce many isomers are generally undesirable.

N-Fluoro-6-chloropyridinium-2-sulfonate has also been reported as a fluorinating agent which has excellent selectivity for a fluorination position. (Advance Notes of the 14th Meeting of Fluorine Chemistry (Japan), 1989). However, there is a problem in that 6-chloropyridine-2-sulfonic acid, which is a starting material in the synthesis of the fluorinating agent, cannot be produced in a sufficiently high yield.

SUMMARY OF THE INVENTION

The present invention provides a new and very useful class of N-fluoropyridinium-sulfonates and processes for making the same.

These sulfonates are useful as fluorinating agents for introducing a fluorine atom into an organic compound. Such agents exhibit excellent reaction specificity, as desired. Also, such agents are themselves simply and reliably prepared.

These sulfonates are represented by the general formula:

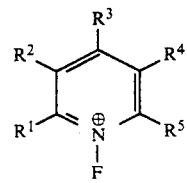

wherein: One of $R^1$ through $R^5$ is $-SO_2O^\ominus$ or -(lower alkylene)$-SO_2O^\ominus$, and the other four are hydrogen atoms.

The compounds of Formula (1) are prepared by reacting fluorine under liquid phase contacting conditions with a pyridinesulfonate having the general formula:

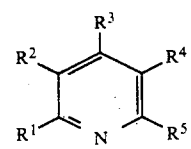

wherein:
a) one of $R^1$ through $R^5$ is $-SO_2OM$ or -(lower alkylene)$-SO_2OM$, and the other four are hydrogen atoms;
b) M is hydrogen atom, ammonium, or alkali metal.

The N-fluoropyridinium-sulfonates are readily and simply prepared using, if desired, commercially available starting compounds within the scope of the Formula (2) compounds.

Surprisingly, in view of the foregoing prior art problems, it has been found that the N-fluoropyridinium-sulfonates of the present invention have sufficient reaction activity for use as fluorinating agents in spite of the fact that no electron withdrawing group, such as a chlorine atom, is present as a substituent on the pyridine ring. Moreover, when used as fluorinating agents, the N-fluoropyridinium-sulfonates of this invention provide excellent position selectivity.

For example, the fluorination of phenol using N-fluoropyridinium-3-sulfonate in accordance with the present invention produces o-fluorophenol in a high yield.

Moreover, the fluorination of a steroid with the same agent of this invention selectively produces 6-fluorosteroid under mild reaction conditions.

Other and further advantages, features, aims, purposes, objects, embodiments, applications, and the like will be apparent to those skilled in the art from the following description of the present invention.

DETAILED DESCRIPTION

The term "lower" as used herein with reference to the term "alkylene" in the definition of substituents for each of the Formula (1) and Formula (2) compounds refers to less than five carbon atoms.

It is advantageous that pyridinesulfonic acid compounds within the scope of Formula (2) are commercially available. Examples of suitable starting compounds within the scope of the Formula (2) compounds include 2-pyridinesulfonic acid, 3-pyridinesulfonic acid, 4-pyridinesulfonic acid, lithium 2-pyridinesulfonate, sodium 2-pyridinesulfonate, potassium 2-pyridinesulfonate, sodium 3-pyridinesulfonate, sodium 4-pyridinesulfonate, ammonium 2-pyridinesulfonate, potassium 2-pyridylethylsulfonate, and the like.

The fluorine gas used as a starting material in the practice of the present invention is preferably diluted with about 99.9 percent to about 50 percent by volume of an inert gas to control the vigorous reaction characteristics of fluorine gas. Examples of suitable inert gases which may be used include nitrogen, helium, argon, mixtures thereof, and the like. The particular amount of fluorine used in any given instance depends upon the method of introduction (or contact with reactant), the reaction temperature, the reaction solvent, the solubility of fluorine in the liquid phase carrier medium used and the reactor use, and the like. However, to achieve high product yields, the total amount of fluorine employed is preferably at least about equimolar relative to the amount of the reactant (i.e., the Formula (2) compound) used.

During the reaction, a starting compound of Formula (2) is colloidally dispersed or preferably dissolved in an inert solvent or carrier liquid. Presently preferred carrier liquids are either mixtures of water with organic polar liquids or such organic liquids alone. One presently preferred organic solvent is acetonitrile, although other organic liquids are also suitable including trichloromethane and methylene chloride.

Convenient weight ratios of water to organic liquid are in the range of about 1:50 to about 1:5, although larger and smaller weight ratios may be used, if desired. A preferred weight ratio of water to organic liquid is about 1:20 to 3:20. Although the reaction temperature can be in the range of about −45 degrees Centigrade (°C.) to about room temperature, a reaction temperature within the range of about −40° C. to about 0° C. is preferred to provide the desired high yields.

As indicated above, the N-fluoropyridinium-sulfonate compounds of Formula (1) are easily produced and have excellent position selectivity when used as fluorinating agents. In addition, after reacting as fluorinating agents, these agents reproduce the pyridinesulfonic acid, which is a raw material for producing these agents. Therefore, it can be said that these agents have extremely high availability in the industrial field.

One presently preferred class of Formula (1) compounds comprises those made from commercially available pyridinesulfonic acid compounds of Formula (2). Fluorinating agents of Formula (1) prepared therefrom in accordance with this invention can be made on an economical basis in relatively large quantities, as is desired for commercial production.

EMBODIMENTS

The present invention is illustrated by the following examples:

EXAMPLE 1:

Preparation of N-Fluoropyridinium-2-sulfonate

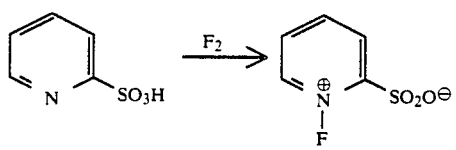

2-Pyridinesulfonic acid [477 mg (3.0 mmol)] was dissolved in 6.6 ml of a solvent mixture containing water and acetonitrile (1:10), and the resultant solution was then cooled to −25° C. A gas mixture containing fluorine gas and nitrogen gas (1:9) was then introduced into the solution at a flow rate of 40 ml/min under agitation so that a reaction took place. The amount of the fluorine introduced was 9 mmol. After the reaction, 20 ml of tetrahydrofuran was added to the reaction solution, and the resultant mixture was then warmed to room temperature. The separated crystals were filtered off and dried to provide 427 mg of N-fluoropyridinium-2-sulfonic acid in a yield of 81 percent. The values of physical properties and the spectral data are as follows:

Decomposition point: 232°–235° C.

$^{19}$F-NMR (CFCl$_3$ internal standard in heavy acetonitrile): −41.2 ppm (bs, NF).

$^1$H-NMR (400 MHz, in heavy acetonitrile): δ8.11 (1H, m, 5-H); 8.50 (1H, ddd, J=7.6, 6.5, 2.2 Hz, 3-H); 8.61 (1H, tdd, J=7.6, 1.5, 1 Hz, 4-H); and 9.04 (1H, ddd, J=14.5, 7.0, 1 Hz, 6-H).

Mass; m/e 177 (M+).

| Elemental analysis value: | | | |
|---|---|---|---|
| | C | H | N |
| Measured value: | 33.98% | 2.28% | 7.95% |
| Calculated value: | 33.90% | 2.28% | 7.91% |

EXAMPLE 2:

Preparation of N-Fluoropyridinium-2-sulfonate

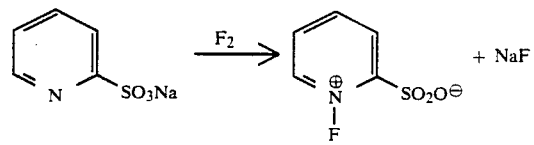

Sodium 2-pyridinesulfonate (1 mmol) was added to 2.2 ml of a solvent mixture containing water and acetonitrile (1:10). A gas mixture containing fluorine gas and nitrogen gas (1:9) was then introduced into the resultant mixture at −25° C. and at a flow rate of 30 ml/min. The amount of the fluorine introduced was 9 mmol. After the reaction, 20 ml of tetrahydrofuran was added to the reaction solution, and the separated precipitate was filtered off. The thus-formed precipitate was extracted with acetonitrile, and the solvent was then removed by distillation to provide 68 mg (38 percent) of N-fluoropyridinium-2-sulfonate. The spectral data of the product was the same as that obtained in Example 1.

REFERENCE EXAMPLE 1

Preparation of o-Fluorophenol from Phenol and N-Fluoropyridinium-2-sulfonate

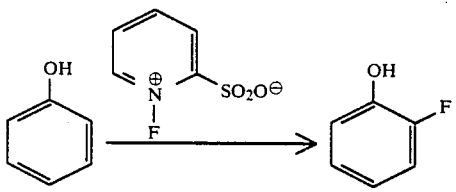

A mixture containing 2 ml of dry 1,1,2-trichloroethane, 53.0 mg (0.56 mmol) of phenol and 99.7 mg (0.56 mmol) of N-fluoropyridinium-2-sulfonate was refluxed in an argon atmosphere for 1.5 hours. When the reaction solution was quantitatively analyzed by gas chromatography, it was determined that 0.252 mmol (conversion yield: 56 percent) of o-fluorophenol was produced, with 0.106 mmol (19 percent) of unreacted phenol. p-Fluorophenol and 2,4-difluorophenol were not detected.

REFERENCE EXAMPLE 2

Preparation of 6-Fluoro-4-androstene-17β-ol-3-one from 3,17β-bis(trimethylsilyloxy)-3,5-androstadiene and N-Fluoropyridinium-2-sulfonate

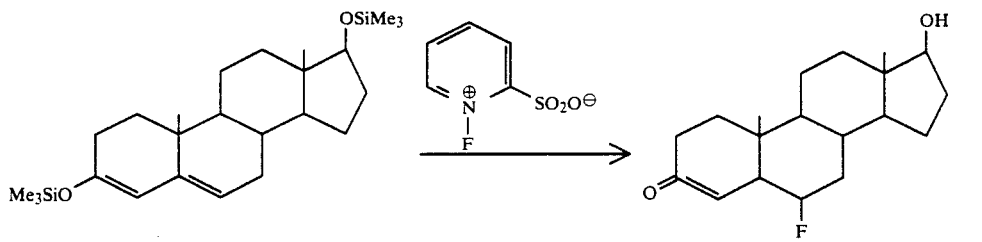

A mixture containing 10 ml of dry methylene chloride, 1033 mg (2.39 mmol) of 3,17β-bis(trimethylsilyloxy)-3,5-androstadiene and 426 mg (2.39 mmol) of N-fluoropyridinium-2-sulfonate was agitated for 49 hours at room temperature in an atmosphere of argon. After the product had been treated by a normal method, it was purified by column chromatography to obtain 299 mg of 6-fluoro-4-androstene-17β-ol-3-one in a yield of 41 percent.

The spectral data of the product was the same as that of the standard sample. Trace amounts of 4-fluoro-5-androstene-17β-ol-3-one, which was produced by fluorination at the 4-position, were observed in the $^{19}$F-NMR spectrum of the crude reaction product before purification. With regard to the three-dimensional configuration of the fluorine atom at the 6-position, the α/β ratio of the product obtained was $\frac{1}{3}$.

While the present invention has been described with reference to particular embodiments, it will be understood that various changes and modifications can be made, as will be apparent to those skilled in the art, without departing from the spirit thereof. No undue limitations should be assumed or made in the scope of the foregoing description and the following claims.

What is claimed is:

1. N-Fluoropyridinium-sulfonates of the formula:

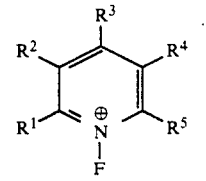

wherein:
one of $R^1$ through $R^5$ is $-SO_2O^\ominus$ or -(lower alkylene)$-SO_2O^\ominus$, and the other four are hydrogen atoms.

2. N-Fluoropyridinium-2-sulfonate.

3. A process for making N-fluoropyridinium-sulfonates comprising contacting dilute gaseous fluorine with a solution of a compound of the formula:

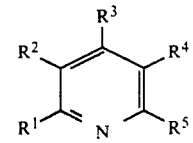

wherein:
a) one of $R^1$ through $R^5$ is $-SO_2OM$ or -(lower alkylene)$-SO_2OM$, and the other four are hydrogen atoms;
b) M is hydrogen atom, ammonium, or alkali metal.

* * * * *

UNITED STATES PATENT AND TRADEMARK OFFICE
CERTIFICATE OF CORRECTION

PATENT NO. : 5,081,249

DATED : January 14, 1992

INVENTOR(S) : Teruo Umemoto

It is certified that error appears in the above-identified patent and that said Letters Patent is hereby corrected as shown below:

On the Title page, item [57], col. 2, line 2,
ABSTRACT, line 2, "processw" should read --process--;

Column 1, lines 36-37, "6-flouros-teroid" should read
--6-fluoro-steroid--;

Column 2, lines 49-50, "6-flouros-teroid" should read
--6-fluoro-steroid--;

Column 4, lines 65-66, "1,1,2-trichloroe-thane" should read
--1,1,2-trichloro-ethane--;

UNITED STATES PATENT AND TRADEMARK OFFICE
CERTIFICATE OF CORRECTION

PATENT NO. : 5,081,249
DATED : January 14, 1992
INVENTOR(S) : Teruo Umemoto

It is certified that error appears in the above-identified patent and that said Letters Patent is hereby corrected as shown below:

Columns 5 and 6, " 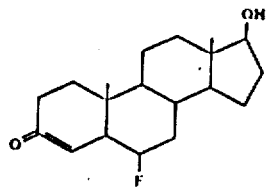 " should read

-- 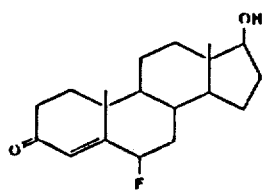 -- and should be located under the yield symbol in Column 5.

Column 5, line 41, "$\frac{1}{3}$" should read --1/3--.

Signed and Sealed this

Ninth Day of November, 1993

Attest:

Attesting Officer

BRUCE LEHMAN

Commissioner of Patents and Trademarks